United States Patent [19]

Hooker

[11] Patent Number: 5,062,424
[45] Date of Patent: Nov. 5, 1991

[54] PORTABLE APPARATUS FOR RAPID REDUCTION OF ELEVATED BODY CORE TEMPERATURE

[75] Inventor: Daniel N. Hooker, Chapel Hill, N.C.

[73] Assignee: The University of North Carolina at Chapel Hill, Chapel Hill, N.C.

[21] Appl. No.: 645,218

[22] Filed: Jan. 24, 1991

[51] Int. Cl.$^5$ ............................................. A61F 7/00
[52] U.S. Cl. ................................. 128/379; 128/400; 62/259.3; 2/81
[58] Field of Search ........................... 2/2, 7, 8, 69, 81; 165/46; 62/259.3, 237; 128/379, 380, 373, 375, 367, 371, 399, 900, 902, 201.29, 202.13, 202.11, 202.12, 202.19; 4/536, 535; 126/204

[56] References Cited

U.S. PATENT DOCUMENTS

| | | |
|---|---|---|
| 630,565 | 8/1899 | Safran . |
| 2,093,834 | 9/1937 | Gaugler ............................ 128/145 |
| 2,255,751 | 9/1941 | Bancel . |
| 2,319,542 | 5/1943 | Hall ................................... 128/400 |
| 2,413,386 | 12/1946 | Schulz ........................... 128/201.29 |
| 2,415,955 | 2/1947 | Bames et al. ...................... 128/399 |
| 2,984,994 | 5/1961 | Hankins .............................. 62/259.3 |
| 3,468,299 | 9/1969 | D'Amato ............................ 126/204 |
| 3,496,703 | 2/1970 | MacLeod .......................... 62/259.3 |
| 3,885,571 | 5/1975 | Sachs ................................. 128/400 |
| 3,908,655 | 9/1975 | Lund .................................. 128/375 |
| 3,916,911 | 11/1975 | Sauder et al. ....................... 62/259.3 |
| 4,055,173 | 10/1977 | Knab ............................. 128/201.29 |
| 4,146,933 | 4/1979 | Jenkins et al. ............................ 2/2 |
| 4,251,994 | 2/1981 | Reinhom ............................... 82/237 |
| 4,867,230 | 9/1989 | Voss .................................... 165/46 |
| 4,914,752 | 4/1990 | Hinson et al. ............................ 2/2 |
| 4,998,414 | 3/1991 | Tomlmatsu ....................... 62/259.3 |

FOREIGN PATENT DOCUMENTS

799972 1/1981 U.S.S.R. ............................ 62/259.3

Primary Examiner—Edward M. Coven
Assistant Examiner—Mark S. Graham
Attorney, Agent, or Firm—Richard E. Jenkins

[57] ABSTRACT

A portable apparatus for rapid on-site reduction of elevated body core temperature for use by individuals suffering from heat stress induced by activity in a hot, humid environment. The apparatus comprises a transportable housing having an air conditioner mounted therein and a hooded, cooling garment removably stored within the housing. A plurality of flexible air supply hoses serve to fluidly connect the air condition to the garment when the garment is removed from the housing for use.

20 Claims, 3 Drawing Sheets

PORTABLE APPARATUS FOR RAPID REDUCTION OF ELEVATED BODY CORE TEMPERATURE

DESCRIPTION

1. Field of the Invention

The present invention relates to air conditioned garments and, more particularly, to a portable apparatus for use by athletes, fire fighters, workers and others in hot environments to rapidly reduce elevated core body temperature to a safe level.

2. Description of the Related Art

Body overheating through vigorous participation in sports and job-related activities is a widely recognized problem which is particularly of concern in hot, humid climates where human body temperature substantially in excess of safe levels can occur. This type of body overheating can result in enforced periods of inactivity and, in many cases, may require treatment such as soaking an overheated person in cool water or immersion of the person in an ice bath. In the most extreme instances, hospitalization of the individual may result.

As is well known to those familiar with football and similar rigorous sports, there are unfortunate incidents of heat-related deaths every year among groups of individuals who otherwise are recognized as exceptionally physically fit. Many other less severe forms of heat illness also occur and can result in significant health hazards to the individuals involved and attendant losses in training and playing time. These same problems are also inherent in other fields of human endeavor where the individual is exposed to a hot, humid environment.

Avoidance of body overheating stress is normally accomplished with scheduled rest periods, particularly among individuals previously recognized as susceptible to heat stress. Unfortunately, many times such rest periods may be incompatible with athletic game participation or work requirements and/or may be disregarded as unnecessary by an aggressive athlete or worker. Failure to cool down sufficiently during rest periods may consequently then lead to progressive rises in body temperature which can ultimately reach dangerous levels that require off-site treatment and medical intervention. Applicant's invention was developed to address these well recognized problems associated with heat stress in athletes as well as workers and other individuals who must perform in a hot, humid environment for an extended period of time.

Applicant is aware of certain previous efforts to address the heat stress problem encountered by athletes and others performing in a hot, humid environment. For example, "side-line air conditioning" or air conditioners mounted on rollers and provided with an air duct on the front thereof have been used at athletic events to cool the players. Typically, the air conditioner is rolled into a position close to the players' bench at a football game and/or rolled into the locker rooms for cooling. This type of apparatus has been used at a number of institutions including Georgia Institute of Technology and North Carolina State University. Similarly, applicant is aware of the use of an air conditioned clear cellophane tent to accommodate multiple athletes on the side-lines at the University of Georgia in Athens, Georgia.

With respect to other related art, U.S. Pat. No. 3,468,299 to D'Amato discloses an air conditioned hooded garment formed from a suitable coat fabric and provided with an interior perforated plastic lining within the upper portion of the coat and hood. A pair of portable, battery powered air fans are positioned beneath the coat to provide air flow to the space defined between the perforated lining and the coat fabric. The air flow escapes inwardly through the perforations in the lining to lower the temperature within the coat and hood before eventually passing therefrom to the atmosphere. The garment is intended to assure the comfort of the user in an extremely adverse environment.

U.S. Pat. No. 4,914,752 to Henson et al. is directed to a temperature regulated garment for use by persons who work in environments containing toxic or dangerous chemicals. The garment comprises an outer protective layer of a low air-permeable material and an inner layer formed of an air-permeable porous material. An attached vortex tube connected to a remote compressed air source provides air to the space defined between the outer and inner layers which then passes through the air permeable diffuser inner layer into the body surrounding area of the garment. In this fashion, the air flow serves to cool the individual wearing the garment and prevent hazardous chemicals from entering.

Also of note, U.S. Pat. No. 4,146,933 to Jenkins et al. discloses an air conditioned suit and system which includes air conditioning hose connections at both the front left and front right sides as well as at the rear of the suit for connection of an air hose at a suitable singular location in view of the intended use of the suit.

SUMMARY OF THE INVENTION

In accordance with the present invention, applicant provides a portable apparatus for rapid reduction of elevated body core temperature of an overheated person. The apparatus comprises a container housing movably mounted on a plurality of wheels. An air conditioner is mounted in the container housing, and a garment having an interior and an exterior surface and comprising a head covering and a torso covering portion is also removably stored therein. A plurality of flexible air supply hoses fluidly communicate at one end with the air conditioner and at the other end with the interior surface of the garment in order to convey cool air flow from the air conditioner to the garment. In use, the apparatus provides for rapid cooling of a person wearing the garment by the combination of a cooled environment and a rapid air flow past the body surface which enhances the natural body evaporative cooling mechanism.

It is therefore the object of this invention to provide a portable apparatus for rapid on-site reduction of elevated body core temperature of an overheated person.

It is another object of the present invention to effect a rapid cooling of a person who has reached a point of discomfort in a hot, humid environment and to allow the person to quickly return to previous activity.

It is another object of the present invention to cool athletes in hot, humid environments and to help reduce the incidence of heat exhaustion and/or heat stroke caused by heat stress.

It is still another object of the present invention to provide a portable apparatus for cooling football layers and other athletes which provides more effective cooling than conventional cooling techniques and allows for enhanced performance in high heat and high humidity playing conditions.

Some of the objects of the invention having been stated, other objects will become evident as the description proceeds, when taken in connection with the accompanying drawings which ar described below.

BRIEF DESCRIPTION OF THE DRAWINGS

FIG. 3B is an enlarged, fragmentary elevation view of the clamp ring connections of a flexible tube to the garment and manifold at opposing ends thereof.

DETAILED DESCRIPTION OF THE INVENTION AND PREFERRED EMBODIMENT THEREOF

Figure 1:
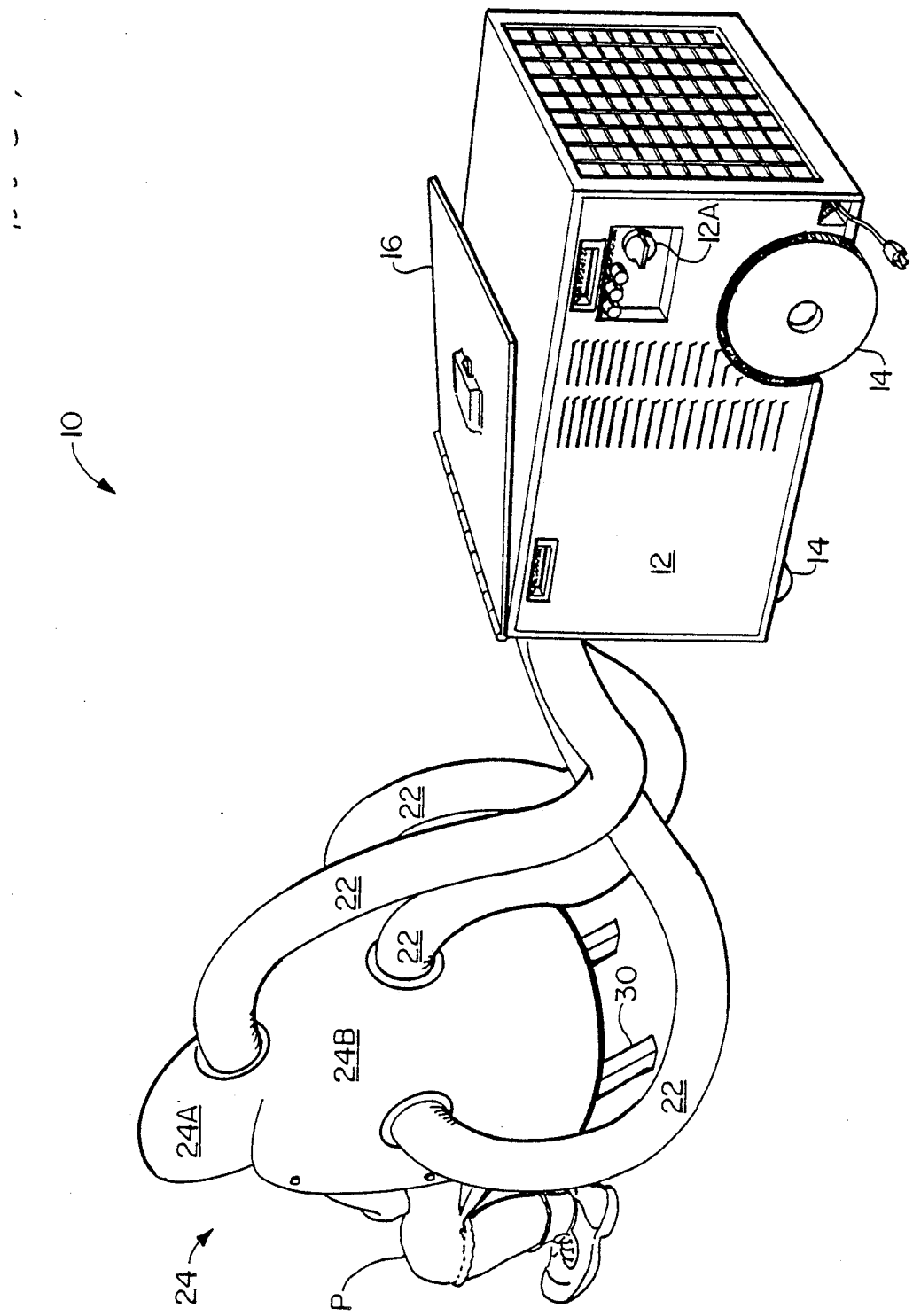
FIG. 1 is a perspective view of a person using a portable cooling apparatus constructed in accordance with the principles of the present invention.

Referring now to FIGS. 1-5 of the drawings, applicant's portable apparatus for rapid reduction of elevated body core temperature is generally designated 10. Apparatus 10 comprises a cabinet 12, preferably constructed from sheet steel. Although substantially any size cabinet may be utilized, applicant presently contemplates that cabinet 12 will have a maximum height of 25.50 inches, a maximum width of 27.00 inches and a maximum length of 39.00 inches.

Cabinet 12 is mounted for easy movement on four wheels 14. Most suitably, wheels 14 are about 4-6 inches in diameter for easy rolling movement over turf and other ground surfaces, and front wheels 14 are swivel wheels whereas back wheels 14 are fixed wheels. This preferred configuration of wheels 14 allows for easy manual rolling and direction of cabinet 12.

A hinged door 16 is mounted to the front of cabinet 12 in order to provide access to the interior thereof. Mounted within the back of cabinet 12 is a conventional room air conditioner 18 with the controls therefor provided in control panel 12A mounted to the exterior of cabinet 12. Although applicant contemplates that many different types of commercial window air conditioning units may be utilized by apparatus 10 of the invention, applicant prefers a 110 volt air conditioner providing between about 8,000 to 14,000 B.T.U.'s of cooling capacity. For example, applicant has found that a Whirlpool brand (Model Nos. AC 1002-XS 10,000 B.T.U. and AC 1202-XS 12,000 B.T.U.) 110 volt air conditioner works particularly well in prototypes constructed in accordance with the present invention.

Figure 4:
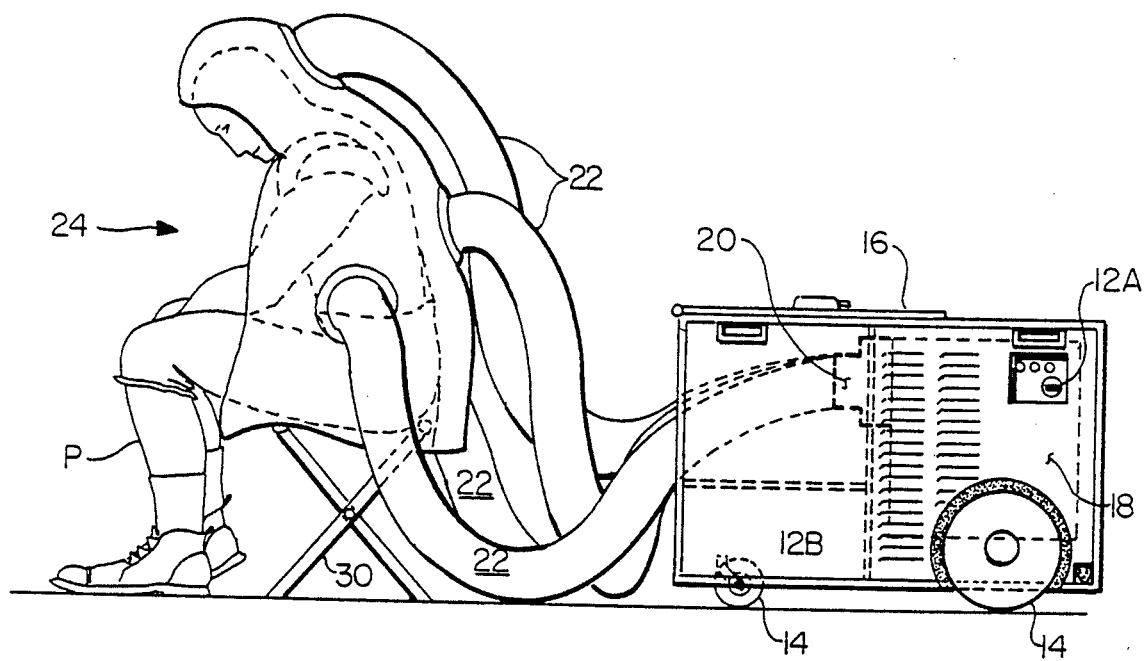
FIG. 4 is a side elevation view of a portable apparatus for rapid cooling according to the present invention with the garment and flexible air supply hoses removed from storage therein and placed in use.
Figure 5:
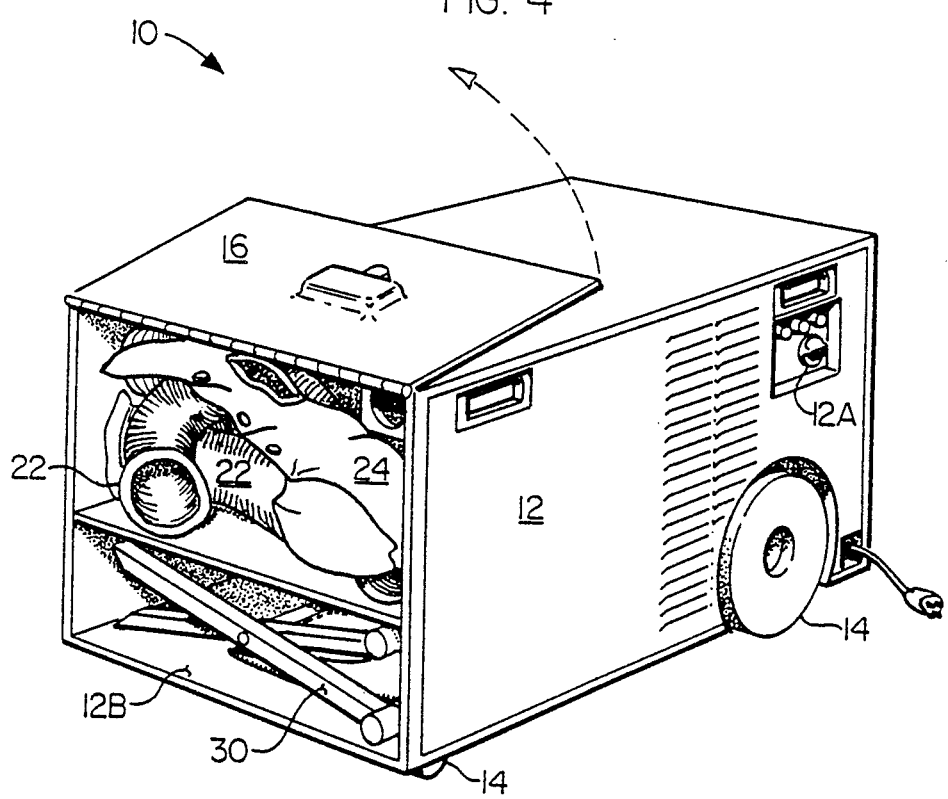
FIG. 5 is a perspective front view of a portable apparatus according to the present invention with the garment and flexible air supply hoses stored therein prior to closure of the hinged door of the cabinet.

As best seen in FIG. 4 of the drawings, a plastic manifold 20 is mounted to the front of air conditioner 18 so as to encompass all of the cool air exhaust vents thereof (not shown). Four flexible and linearly collapsible hoses 22 are each removably connected at one end to manifold 20 and at the other end to cooling garment 24. Although applicant believes that many different types of flexible and linearly collapsible hoses may be utilized, applicant presently prefers a linearly collapsible plastic hose having a diameter between about 2 to 4 inches and a fully extended length of about 5 to 15 feet. Most suitably, applicant has found that a 3 inch diameter and 6-8 foot long fully extended hose 22 works particularly well in a developmental prototype of apparatus 10.

Flexible hoses 22 are removably connected at one end to manifold 20 and the other end to cooling garment 24 by any suitable releasable fastening mechanism. For example, with reference now to FIGS. 3A and 3B, hose 22 may be releasably attached at each end to manifold 20 and cooling garment 24, respectively, by VELCRO surfaces V provided at each end thereof for releasable engagement to mating VELCRO surfaces VV adjacent corresponding manifold aperture 20A and cooling garment aperture 24A (see FIG. 3A). The opposing ends of hose 22 are releasably attached so as to provide for fluid communication from manifold 20 through flexible hose 22 and finally into the inside of cooling cape 24. Alternatively, and with reference to FIG. 3B, applicant contemplates that a clamp ring-type connector C could be used to removably connect flexible tube 22 to manifold 20 and cooling cape 24 as well as other easy-to-use connector mechanisms such as a twist-connect attachment (not shown). Clamp ring connector C shown in FIG. 3B comprises a resilient ring C' for releasably securing each end of hose 22.

Figure 2:
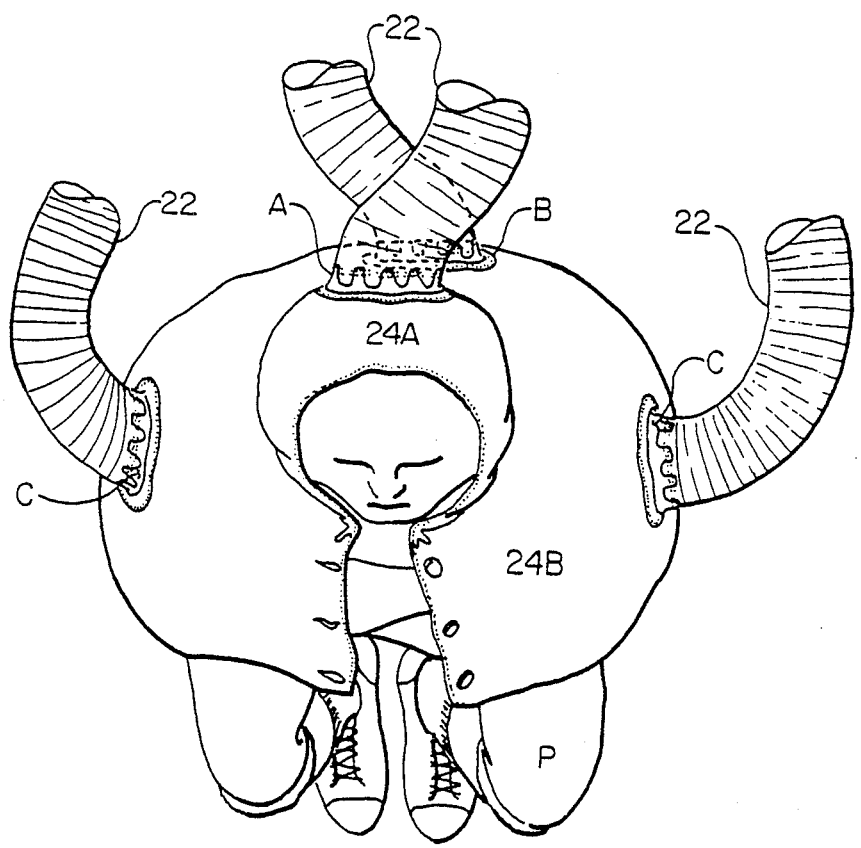
FIG. 2 is a top plan view of the garment and flexible tubes of the portable apparatus of the present invention.
Figure 3A:
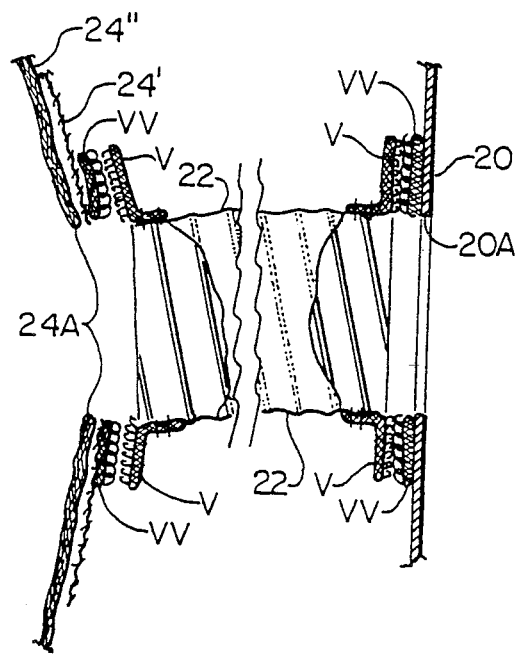
FIG. 3A is an enlarged, fragmentary elevation view of the VELCRO connections of a flexible tube to the garment and manifold at opposing ends thereof.
Figure 3A:
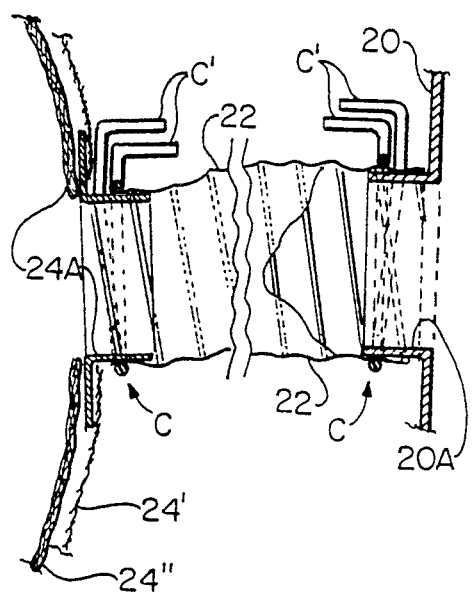

With particular reference to FIGS. 1, 2 and 4 of the drawings, a better appreciation can be had of cooling garment 24 and the specific connector locations of four flexible hoses 22 connected thereto. Cooling garment 24 most suitably comprises a hood 24A and a torso-covering section 24B which is designed to be loosely wrapped around a person or wearer P requiring the benefit of cool air flow to alleviate heat distress. Person P pulls the front of cooling garment 24 shut so as to enclose his body in cooling garment 24 to provide a cooling environment for quick recovery from increased body temperature. Thus, portable apparatus 10 provides for rapid cooling of the body by concentration of cool, dry air flow to the body surface to cool the body of person P by both convection and evaporation. The cooling air flow passing between the inside surface of cooling garment 24 and the body of wearer P generally exhausts from the open bottom of the garment. As best seen in FIGS. 3A and 3B, cooling garment 24 is formed from an outer layer 24' (preferably nylon fabric) and an inner insulating layer 24" (preferably a non-woven batting fabric). Outer layer 24' and inner insulating layer 24" may be suitably secured together by any conventional garment fabrication method.

With reference again to FIG. 2 of the drawings, it can be seen that flexible hoses 22 are removably connected to cooling garment 24 at the following locations: (A) at the back of hood 24A of cooling garment 24; (B) at the back of torso covering portion 24B of cooling garment 24; and (C) at each side of torso covering portion 24B of cooling garment 24 in the proximate area of the kidneys of wearer P of cooling garment 24. These specific locations for connection of flexible hoses 22 to cooling garment 24 have been found to be critical since they provide for maximum efficiency of the cooling air flow to wearer P. More specifically, the aforementioned connections provide for air flow to the back of the head, to the kidney area, and to the medial back area of wearer P. This has been found to enhance the cooling effect of cool air flow on body core temperature due to significant body blood flow proximate to these specific sites of air flow introduction to cooling garment 24.

Thus, portable apparatus 10 serves to direct a powerful current of low humidity, cooled air to the back of the neck, to the middle of the back, and to the regions near the kidneys of person P wearing cooling garment 24 while either in a seated or a standing position. Applicant's preferred embodiment of portable apparatus 10 includes providing a storage compartment 12B in cabinet 12 where a collapsible stool 30 may be stored for removal and use when apparatus 10 is rolled to a site for use (see FIGS. 4 and 5). At the use site, hinged door 16 would be opened and cooling garment 24 and collapsible stool 30 removed from cabinet 12 for use by the individual suffering from heat stress. Although a primary use for portable apparatus 10 is contemplated to be for administering to football players at the side-line of the field, other uses for the invention include military training camps, heavy construction sites, marathon races, and as part of the equipment of emergency rescue vehicles.

The efficacy of portable apparatus 10 has been tested and proven during experimentation with a prototype. As is well known to those familiar with heat stress health problems, a core body temperature of 101° F. results in activation of the sweat glands in an effort to cool the body. Prolonged sweating results in heat exhaustion and a body core temperature of greater than 106° F. can result in heat stroke. Most suitably, applicant contemplates that portable apparatus 10 will be used whenever an athlete or worker in a hot, humid environment has a core temperature above 101° F. and that the individual will be maintained within cooling garment 24 until his core body temperature drops into the 99° F. to 100° F. range.

Typically, human body core temperature begins to drop within about two minutes after an individual is placed within cooling garment 24 and air conditioner 18 is actuated. The individual is maintained within cooling garment 24 for about five minutes until his core body temperature drop to about 89.9° F. or 99° F. This has been found to be much more effective than conventional cooling methodology including drinking cold water and applying ice towels to the shoulders of an athlete or other individual suffering from heat stress.

Representative results from testing of a prototype of portable apparatus 10 are set forth in Examples 1 and 2 below.

EXAMPLE 1

A football player in scrimmage suffered from heat stress. His body core temperature was reduced from 103° F. to 98° F. after five minutes of treatment with portable apparatus 10.

EXAMPLE 2

A football player suffered symptoms of heat distress during football scrimmage including overheating, dizziness, fatigue and flushed skin appearance. The player's body core temperature was 101.5° F. when subjected to treatment by portable apparatus 10. The individual's core body temperature fell to 99.5° F. in two minutes, 99.0° F. in three minutes and 98.5° F. in four minutes.

It will be understood that various details of the invention may be changed without departing from the scope of the invention. Furthermore, the foregoing description is for the purpose of illustration only, and not for the purpose of limitation——the invention being defined by the claims.

What is claimed is:

1. A manually rolled portable apparatus for rapid cooling of an overheated person comprising:
    a container housing movably mounted on a plurality of wheels;
    air conditioning means mounted in said container housing for providing a cool air flow;
    a garment with an interior and an exterior surface removably stored within said container housing and comprising at least a head covering portion and a torso covering portion; and
    a plurality of flexible air supply hoses fluidly communicating at one end thereof with said air conditioning means and at the other end thereof with the interior surface of said garment.

2. A portable apparatus according to claim 1 wherein said container housing includes a hinged door for access to said stored garment.

3. A portable apparatus according to claim 2 wherein said container housing is mounted on a plurality of swivel wheels at one end thereof and a plurality of fixed wheels at the other end thereof.

4. A portable apparatus according to claim 1 wherein said air conditioning means comprises a 110 volt air conditioner with a cooling capacity rating of between about 8,000–14,000 B.T.U. and an electrical plug for connection to a suitable power source.

5. A portable apparatus according to claim 4 wherein said container housing provides externally accessible controls for operating said air conditioner.

6. A portable apparatus according to claim 1 wherein said garment includes a hood and an upper body covering section and comprises a nylon fabric outer layer and a nonwoven fabric insulating inner layer.

7. A portable apparatus according to claim 6 wherein said plurality of air supply hoses comprises four hoses connected, respectively, to the back of the hood, to the back of the upper body covering section, and to each side of the upper body covering section.

8. A portable apparatus according to claim 6 wherein said air supply hoses are removably attached at each end thereof to said air conditioning means and said garment, respectively, and have a diameter between about 2–4 inches and an extended length of between about 5–15 feet.

9. A manually rolled portable apparatus for rapid cooling of an overheated person comprising:
    a container housing movably mounted on a plurality of wheels;
    air conditioning means mounted in said container housing for providing a cool air flow;
    a garment with an interior and an exterior surface removably stored within said container housing and comprising a hood and a torso covering portion; and
    four flexible air supply hoses fluidly communicating at one end thereof with said air conditioning means and at the other end thereof with the interior surface of said garment, said four air supply hoses being connected, respectively, to the back of the hood, to the back of the torso covering portion, and to each side of the torso covering portion of said garment.

10. A portable apparatus according to claim 9 wherein said container housing includes a hinged door for access to said stored garment.

11. A portable apparatus according to claim 10 wherein said container housing is mounted on a plurality of swivel wheels at one end thereof and a plurality of fixed wheels at the other end thereof.

12. A portable apparatus according to claim 9 wherein said air conditioning means comprises a 110 volt air conditioner with a cooling capacity rating of between about 8,000-14,000 B.T.U. and an electrical plug for connection to a suitable power source.

13. A portable apparatus according to claim 12 wherein said container housing provides externally accessible controls for operating said air conditioner.

14. A portable apparatus according to claim 9 wherein said garment comprises a nylon fabric outer layer and a nonwoven fabric insulating inner layer.

15. A portable apparatus according to claim 9 wherein said air supply hoses are removably attached at each end thereof to said air conditioning means and said garment, respectively, and have a diameter between about 2-4 inches and an extended length of between about 5-15 feet.

16. A manually rolled portable apparatus for rapid cooling of an overheated person comprising:
- a container housing movably mounted on a plurality of wheels and including a hinged door for access to the interior thereof;
- an air conditioner mounted in said container housing for providing a cool air flow;
- a garment with an interior and an exterior surface removably stored within said container housing and behind said hinged door and comprising a hood and a torso covering portion; and
- four flexible and linearly extendible air supply hoses fluidly communicating at one end thereof with said air conditioner and at the other end thereof with the interior surface of said garment, said four air supply hoses being removably connected, respectively, to the back of the hood, to the back of the torso covering portion, and to each side of the torso covering portion of said garment, and having a diameter between about 2-4 inches and an extended length of between about 5-15 feet.

17. A portable apparatus according to claim 16 wherein said air conditioner comprises a 110 volt air conditioner with a cooling capacity rating of between about 8,000-14,000 B.T.U. and an electrical plug for connection to a suitable power source.

18. A portable apparatus according to claim 16 including an air manifold secured to said air conditioner and said four air supply hoses being removably connected thereto at said air conditioner fluid communication ends thereof.

19. A portable apparatus according to claim 16 wherein said garment comprises a nylon fabric outer layer and a nonwoven fabric insulating inner layer.

20. A portable apparatus according to claim 16 wherein said container housing includes a collapsible stool removably stored therein.

* * * * *